United States Patent
Roy et al.

(10) Patent No.: US 11,639,932 B2
(45) Date of Patent: May 2, 2023

(54) APPARATUS FOR PRECONCENTRATING AND TRANSFERRING ANALYTES FROM SURFACES AND MEASUREMENT THEREOF USING SPECTROSCOPY

(71) Applicant: Orono Spectral Solutions, Inc., Bangor, ME (US)

(72) Inventors: Eric Roy, Lisbon Falls, ME (US); Rachel Gettings, Bangor, ME (US); Luke Doucette, Hampden, ME (US)

(73) Assignee: Orono Spectral Solutions, Inc., Hermon, ME (US)

( * ) Notice: Subject to any disclaimer, the term of this patent is extended or adjusted under 35 U.S.C. 154(b) by 214 days.

(21) Appl. No.: 17/208,891

(22) Filed: Mar. 22, 2021

(65) Prior Publication Data

US 2021/0389317 A1 Dec. 16, 2021

Related U.S. Application Data

(63) Continuation-in-part of application No. 16/016,993, filed on Jun. 25, 2018, now abandoned, which is a
(Continued)

(51) Int. Cl.
| | |
|---|---|
| *G01N 33/543* | (2006.01) |
| *G01N 1/02* | (2006.01) |
| *G01N 21/3563* | (2014.01) |
| *G01N 1/04* | (2006.01) |
| *B01L 3/00* | (2006.01) |

(Continued)

(52) U.S. Cl.
CPC ......... *G01N 33/54373* (2013.01); *G01N 1/02* (2013.01); *G01N 1/04* (2013.01); *G01N 21/3563* (2013.01); *B01L 3/5029* (2013.01); *G01N 21/552* (2013.01); *G01N 2001/028* (2013.01);
(Continued)

(58) Field of Classification Search
CPC ...... G01N 33/54373; G01N 1/02; G01N 1/04; G01N 21/3563; G01N 21/552; G01N 2001/028; G01N 2001/045; G01N 2021/3595; G01N 21/658; G01N 2001/2826; G01N 2021/1704; G01N 1/405; G01N 21/35; G01N 1/2214; B01L 3/5029; B01L 3/508
See application file for complete search history.

(56) References Cited

U.S. PATENT DOCUMENTS

2010/0009458 A1* 1/2010 Ohtsuka ............. G01N 21/6428
436/166

* cited by examiner

*Primary Examiner* — Jennifer Wecker
*Assistant Examiner* — Michael Paul Shimek
(74) *Attorney, Agent, or Firm* — Caseiro Burke LLC; Chris A. Caseiro

(57) ABSTRACT

An apparatus for capturing a target analyte in advance of performing spectroscopic analysis to determine the existence of the target analyte from a source contacted with a collection substrate. The collection substrate is fabricated of a material selected to have an affinity for the target analyte, sufficiently transparent in a spectral region of interest and capable of immobilizing the target analyte thereon in a manner that limits scattering sufficient to obscure spectral analysis. The collection substrate may be coated with a material selected to react with, bind to, or absorb the target analyte. The target analyte may be captured to the collection substrate by one or more of wiping, dabbing or swabbing a target analyte carrier with the collection substrate.

9 Claims, 10 Drawing Sheets

Related U.S. Application Data continuation-in-part of application No. 14/884,060, filed on Oct. 15, 2015, now Pat. No. 10,031,136, which is a continuation of application No. 13/416,777, filed on Mar. 9, 2012, now abandoned.

(60) Provisional application No. 61/522,593, filed on Aug. 11, 2011, provisional application No. 61/451,780, filed on Mar. 11, 2011.

(51) Int. Cl.
*G01N 21/552* (2014.01)
*G01N 21/35* (2014.01)

(52) U.S. Cl.
CPC .................. *G01N 2001/045* (2013.01); *G01N 2021/3595* (2013.01)

APPARATUS FOR PRECONCENTRATING AND TRANSFERRING ANALYTES FROM SURFACES AND MEASUREMENT THEREOF USING SPECTROSCOPY

CROSS REFERENCE TO RELATED APPLICATIONS

The present application is a continuation and claims the priority benefit of U.S. patent application Ser. No. 16/016,993 filed Jun. 25, 2018, assigned to a common assignee, which is a continuation-in-part and claims the priority benefit of US patent application Ser. No. 14/884,060 filed Oct. 15, 2015, assigned to a common assignee now U.S. Pat. No. 10,031,136, which is a continuation of U.S. patent application Ser. No. 13/416,777, filed Mar. 9, 2012, assigned to a common assignee, which claimed the priority benefit of, U.S. provisional application Ser. No. 61/451,780, filed Mar. 11, 2011, assigned to a common assignee, and U.S. provisional application Ser. No. 61/522,593, filed Aug. 11, 2011, assigned to a common assignee. The entire contents of the priority applications are incorporated herein by reference.

STATEMENT REGARDING FEDERALLY SPONSORED RESEARCH OR DEVELOPMENT

This invention was made using funds obtained from the US Government (US Army, Contract No. W911SR-10-C-0064), and the US Government therefore has certain rights in this invention.

BACKGROUND OF INVENTION

1. Field of the Invention

This invention relates in general to analytical schemes for transferring, preconcentrating, detecting and measuring target analytes from surfaces or interfaces using spectroscopic methods including optical spectroscopy.

2. Description of the Prior Art

Field measurement of suspected hazardous chemicals is a major challenge in applied analytical chemistry. Substances that would be of high interest include unknown residues on surfaces, for example a residue on a soldier's boot or on a military vehicle that is suspected of being a chemical warfare agent, or a spill of an unknown hazardous chemical presented to a first responder. One tool currently available to soldiers and first responders is a field-portable infrared spectrometer called a Hazmat ID (http://www.smithsdetection.com/HazMatID.php). The Hazmat ID is a ruggedized version of a commercially available Attenuated Total Reflectance (ATR) infrared spectrometer. The Hazmat ID allows a user to identify a number of solid and liquid samples in the field. However, the Hazmat ID requires that the sample is a nearly pure liquid or solid, and that a relatively large amount of pure sample is able to be placed and pressed up against the active sensing window. While this instrument works well for some applications, if a suspect residue is not isolatable or is a thin coating, the instrument will not be presented with adequate sample amounts to make a positive identification, potentially compromising mission operations.

Another example of a currently used field-portable Fourier Transfer Infrared (FTIR) spectrometer (http://www.ahurascientific.com/chemical-explosives-id/products/trudefenderft/index.php) is an intelligently packaged ATR infrared spectrometer designed for measuring suspected target analytes by putting the optical sensing window in contact with the unknown chemical during analysis. However, because the sample is measured in situ, the suspected chemical must exist in high concentrations in order for a positive identification. Furthermore, positive identification is compromised if the substance is on a surface that contains bands in the same region of the infrared spectrum that obscure the measurement. In both of the above examples, adequate analysis of a trace residue on a surface would not be possible because the interfering optical signature of the surface itself would dominate the optical spectrum in which trace level measurement is desired. Another limiting factor for ATR-based measurements is that the target analyte must contact the ATR crystal surface, or minimally reside within 1-20 micrometers of the ATR crystal surface so as to be within the evanescent field extending beyond the crystal surface. Therefore, a roughened, porous or irregular (i.e., not flat) surface having features larger than these dimensions may contain a certain amount of analyte material that is not probed by a contact-based ATR measurement. Other spectroscopy tools and techniques are also employed to detect substances including techniques that do not examine optical characteristics of gathered substances. These other analysis tools experience similar limitations associated with the collection of samples for examination.

In the scientific literature, there are several examples of using cotton-based swabs to collect a target analyte and transfer the analyte to an ATR window for infrared spectroscopy. For example, Nel et. al, 2010 (Vibrational Spectroscopy, Volume 53, pp 64-70) describe using acetone soaked swabs to sample an adhesive residue from pottery. Following sampling, some of the acetone (which contains the adhesive) is deposited onto an ATR crystal and analyzed using infrared spectroscopy. However, in this case and others that describe transferring a bulk solvent, the swab is serving simply as a sorbent means to hold a bulk solvent, which is responsible for dissolving the target analyte. There is nothing novel about the collection device, and it is no different than using standard wet chemical laboratory techniques. These types of examples are significantly different from the proposed invention, which involves the use of designed materials with optimized physical (e.g. high surface areas) and/or chemical (molecular imprinting, tailored surface energy, surface charge, receptors with specific binding sites) and/or electromagnetic (charge, potential, flux) characteristics that result in high affinities for, and effective collection/concentration of, target analytes.

Murthy et al., 1985 (Applied Spectroscopy, Volume 39, Number 5, pp 856-860) and Murthy et. al, 1985 (Applied Spectroscopy, Volume 39, Number 6, pp 1047-1050) describe the transfer of polydimethylsiloxane (PDMS) and artificial body soil (ABS) from cotton fabric to a diamond ATR crystal, which is then analyzed using infrared spectroscopy. In these examples, cotton fabric was treated with ABS to test the efficacy of detergents on cotton fabric and PDMS to characterize a water repellant for the fabric. In both cases, pressure was applied to the cotton fabric to squeeze the ABS and PDMS onto the ATR crystal, much like squeezing water out of a sponge onto the optical window and removing the absorbent material. The pressure simply compresses voids found in the bulk fibrous structure of the cotton fabric, thus excluding the ABS and PDMS from the medium. This is significantly different from the present invention in that this invention uses specifically designed advanced materials with high affinities for analytes of interest including chemicals, biological compounds, and particles. The materials are designed to 1) collect, concentrate, and properly prepare a target analyte and 2) allow for subsequent analysis using spectroscopy without interference or to specifically transfer the chemical to another material that allows for analysis using spectroscopy without interference.

Finally, U.S. Pat. No. 7,808,632 discusses using absorptive materials for gas phase analysis. The present invention is significantly different because the materials used are designed for analysis of solids and liquid residues. What is needed is a better tool and process for capturing analytes in satisfactory concentration and for transferring them for measurement.

SUMMARY OF THE INVENTION

The present invention remedies the indicated problems associated with the prior art and serves as an enabling technology for currently fielded and future detection systems. In essence, the invention described herein can be considered 'smart wipes' that optimally capture and concentrate a target analyte onto a unique collection apparatus designed specifically so that it can either be: 1) analyzed directly by an analyzer without interferences or 2) manipulated so as to facilitate efficient and/or selective transfer of the analyte to a substrate for interference-free detection of the target analyte. The material or materials of the smart wipes are designed to 1) collect, concentrate, and prepare a target analyte and 2) allow for subsequent analysis using spectroscopy, including optical spectroscopy, without interference or requirement to specifically transfer the chemical to another material that allows for analysis using optical spectroscopy without interference and/or other forms of non-optical analysis with negligible sample or substrate degradation and/or negligible obscuring of the target analyte.

This invention relates to a way of collecting, preconcentrating and/or transferring chemical analytes using a collection substrate to then be measured using spectroscopy, including optical spectroscopy. For optical spectroscopy, the system of the invention collects a target analyte and facilitates the transmission, specular reflection, diffuse reflectance, attenuated reflectance, or emission of an optical beam; and photoacoustic emission using spectroscopy; whereas transmission can occur in transmission-absorption or reflection-absorption modes (for example: an optical beam in the ultraviolet (UV), visible, infrared (IR), or X-ray region of the electromagnetic spectrum). The surface of the substrate can react with or capture the target analyte through sorption, chemical reaction, or through physical abrasion and entrapment of the surface bound analyte. After the analyte of interest is collected onto the collection substrate, it is analyzed using optical spectroscopy. For example, the collection substrate can be a flexible material with properties that allow for spectroscopic measurements of an immobilized analyte or a material that facilitates the transfer of the chemical analyte to another substrate amenable for spectroscopic analysis (hereafter referred to as an optical substrate). An optical spectrometer may be used for producing the optical beam that probes the target analyte on the substrate. For example, the spectrometer can be a Fourier transform, dispersive, filterometric, or laser based spectrometer. The change in optical spectrum of the particle allows for measurement of the target analyte.

The invention also relates in general to other analytical tools, such as analytical schemes for transferring, preconcentrating, and detecting and measuring target analytes from surfaces or interfaces using ion mobility spectroscopy (IMS) and mass spectroscopy (MS). The invention described herein can be considered a collection substrate that optimally captures and concentrates a target analyte such as an unknown chemical, powder, or residue of any kind that is to be identified using an analytical tool such as a spectroscope, wherein the collection substrate is designed to then release the captured analyte at a desired moment, the released analyte then being in a gas or aerosol phase that is directed into an IMS and/or MS analytical instrument for detection. The collection substrate can react with or capture the analyte through a chemical reaction, sorption, or through physical abrasion and entrapment of the surface bound analyte. The release of the captured analyte from the collection substrate can be accomplished using any suitable method, including heating the collection substrate, laser ablation, sublimation, air flow through the substrate, air flow over the surface of the substrate, pulsed air, vibration, tapping of any kind, scraping of any kind, gravity, centrifugal forces, electrostatic, magnetic, and any combinations thereof. Once released, the analyte is then transferred into an IMS or MS detection instrument, which can take any of the following forms, but is not limited to: Gas Chromatography (GC)-IMS, IMS-MS, GC-MS, and tandem MS.

The analyte capture and transfer system of the present invention provides an improved tool for detecting analytes. It includes a method for capturing a target analyte and preparing it for spectroscopic analysis, the method comprising the steps of contacting the target analyte with a collection substrate, wherein the collection substrate is made of a material selected to have an affinity for the target analyte, sufficiently transparent in a spectral region of interest and capable of immobilizing the target analyte thereon in a manner that limits scattering sufficient to obscure spectral analysis and inserting the collection substrate including the captured target analyte into a spectroscopy tool. The collection substrate may be coated with a material selected to react with, bind to, or absorb the target analyte. The step of contacting the target analyte with the collection substrate may be achieved by one or more of wiping, pressing or swabbing a target analyte carrier with the collection substrate. The step of contacting the target analyte with the collection substrate may also be achieved by passing the collection substrate through a fluid containing the target analyte. The collection substrate may be a glass fiber membrane having a surface treated to increase its hydrophobic characteristic. The collection substrate may be a membrane having nanoparticles with high affinity for the target analyte. The collection substrate may be formed of a stainless steel mesh material. The collection substrate may be formed of a metal-coated polymer membrane. The method may also include the step of drying the collection substrate with the captured target analyte prior to transferring it to the spectroscopy tool.

The invention also includes a method for capturing a target analyte and preparing it for spectroscopic analysis comprising the steps of contacting the target analyte with a collection substrate, wherein the collection substrate is made of a material selected to have an affinity for the target analyte, transferring the captured analyte from the collection substrate to a second substrate, wherein the second substrate is made of a material sufficiently transparent in a spectral region of interest and capable of immobilizing the target analyte thereon in a manner that limits scattering sufficient to obscure spectral analysis and inserting the second substrate including the transferred target analyte into a spectroscopy tool. The second substrate is an optical substrate that may be fabricated of an IR window material, wherein the optical substrate is at least partially transparent in an infrared region of interest and may be fabricated of ATR crystal material. The optical substrate may also be fabricated of a material that reflects an infrared beam. The second substrate may be at least partially fabricated of a material having a higher affinity for the target analyte than the material used to fabricate the collection substrate. The collection substrate may be coated with a material to facilitate the transfer of the target analyte to the second substrate.

The invention is also a collection substrate for capturing a target analyte from a fluid for spectral analysis, wherein the collection substrate is made of a material selected to have an affinity for the target analyte, sufficiently transparent in a spectral region of interest and capable of immobilizing the target analyte thereon in a manner that limits scattering sufficient to obscure spectral analysis. The invention is also an apparatus for capturing a target analyte from a fluid for spectral analysis including a collection substrate made of a material selected to have an affinity for the target analyte, sufficiently transparent in a spectral region of interest and capable of immobilizing the target analyte thereon in a manner that limits scattering sufficient to obscure spectral analysis and a facilitating housing configured to retain thereto and support the collection substrate. Further, the invention is an apparatus for capturing a target analyte from a fluid and preparing it for spectral analysis, which includes a collection substrate made of a material selected to have an affinity for the target analyte, sufficiently transparent in a spectral region of interest and capable of immobilizing the target analyte thereon in a manner that limits scattering sufficient to obscure spectral analysis and an optical support substrate configured to retain the target analyte from the collection substrate, wherein the optical support substrate is made of a material sufficiently transparent in a spectral region of interest and capable of immobilizing the target analyte thereon in a manner that limits scattering sufficient to obscure spectral analysis.

The invention includes a method for capturing a target analyte located on a surface and preparing it for spectroscopic analysis comprising the steps of contacting the surface including the target analyte with a collection substrate, wherein the collection substrate is made of a material selected to have an affinity for the target analyte, sufficiently transparent in a spectral region of interest and capable of immobilizing the target analyte thereon and inserting the collection substrate including the captured target analyte into a spectroscopy tool. Further, the invention is a method for capturing a target analyte for analysis comprising the steps of contacting the target analyte with a collection substrate, wherein the collection substrate is made of a material selected to have an affinity for the target analyte and capable of immobilizing the target analyte thereon and inserting the collection substrate including the captured target analyte into an analysis tool.

Yet further, the invention is an apparatus for capturing a target analyte located on a surface including a collection substrate made of a material selected to have an affinity for the target analyte and arranged to contact the surface including the target analyte and a facilitating housing configured to retain thereto and support the collection substrate sufficiently to enable analysis of the target analyte on the collection substrate. The apparatus of the invention is also an apparatus for capturing a target analyte located on a surface including a collection substrate made of a material selected to have an affinity for the target analyte and arranged to contact the surface including the target analyte and suitable for use in a target analyte analysis device and a second substrate configured to retain the target analyte from the collection substrate when the collection substrate and the second substrate contact one another, and may further include a facilitating housing configured to retain thereto and support the collection substrate.

The configurations and advantages of the invention will become more apparent upon review of the following detailed description, the accompanying drawings and the appended claims.

DETAILED DESCRIPTIONS OF THE INVENTION

Figure 1:
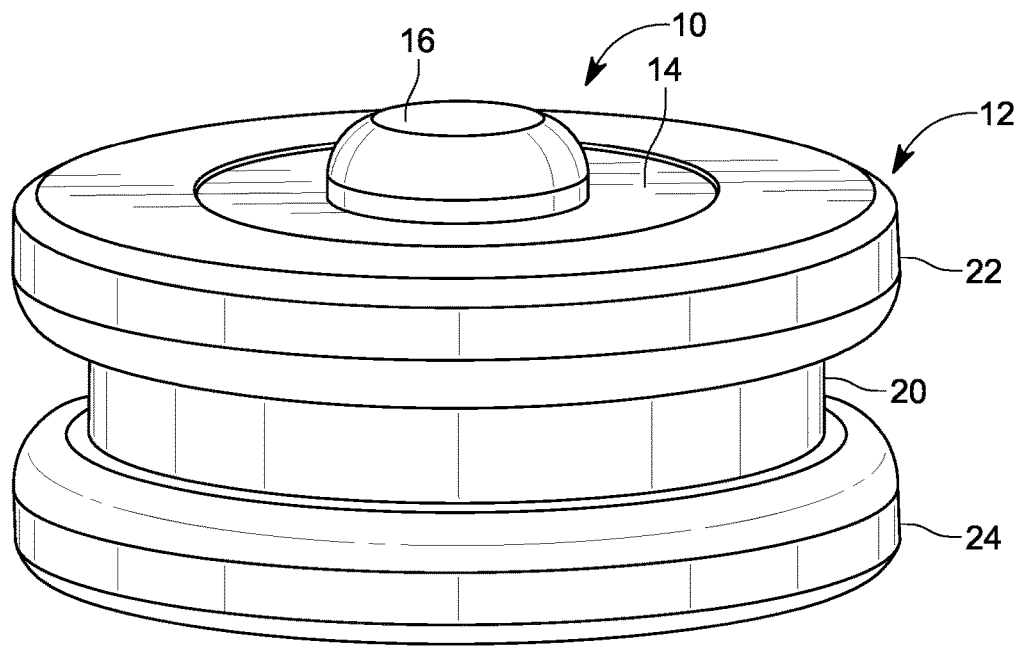
FIG. 1 is a perspective view of an embodiment of the collection substrate of the present invention shown retained to a facilitating housing.

This detailed description of the present invention is primarily directed to consideration of optical spectroscopy analysis tools and analysis methods. However, it is to be understood that the collection arrangement is also suitable for use in non-optical spectroscopy tools and analysis methods including, but not limited to IMS and MS. The detection system of the invention uses a collection substrate that collects and/or concentrates the target analyte through the result of a reaction, sorption or abrasion. Following the target analyte transfer onto the collection substrate, the target analyte can be transferred from the collection substrate to a substrate that facilitates spectroscopy, such as an optical substrate that facilitates optical spectroscopy. In some cases, the collection substrate is formed of a material that is amenable to analysis by a particular type of spectroscopy. In this invention, the collection substrate may be an optical or a non-optical substrate. The analyte to be detected or measured can be any chemical of interest (including, but not limited to PDMS, cyanide, phosphate, explosive residues, crude oil slick, arsenic and VX), biological material (including, but not limited to, DNA, proteins, blood components, spores, bacteria, viruses), and particles (including, but not limited to, clays, organic particles, colloidal material).

The collection substrate can be formed of, or coated with, material that reacts with, binds to, adsorbs or otherwise collects the target analyte. Any suitable material(s) can be used to make or coat the collection substrate, and the collection substrate can be coated using any suitable technique(s) including, for example, physical vapor deposition, spin coating, chemical vapor deposition, precipitation, aggregation, self assembly, Langmuir-Blodgett techniques, electroplating, or atomic layer deposition. Furthermore, particles, colloids, nanoparticles, dissolved reagents, and multiphase reagent delivery vehicles can be impregnated or otherwise attached to the collection substrate. The composition of the collection substrate, film(s), and chemical reagents may depend on the nature of the target analyte(s), the phase or the target analyte's environment, and the type of optical measurement(s) used to measure the change in optical spectrum, if the collection substrate is to be analyzed directly. The collection substrate may be approximately 1 micron to 100 cm in size but may differ from that range as a function of the analysis tool and method employed to detect the target analyte.

The collection substrate is sized and shaped to effectively collect, and if needed, concentrate a target analyte. The collection substrate can be used to collect the target analyte from any surface including, for example, a residue on a solid surface, a target analyte floating on the surface of water or another liquid, or a surface of a bulk liquid. Alternatively, the collection substrate may also be used to collect a target analyte dissolved in water or contained in a gas fluid such as by inserting it into the liquid or gas fluid rather than contacting it with the surface of a solid or a fluid. Types of solid surfaces that may be contacted with the collection substrate include but are not limited to porous, non-porous, flat, non-flat, metal, painted surfaces, plastic, clothing, wood, paper, ceramic, porcelain, and asphalt. Any acceptable method can be used to collect the target analyte onto the collection substrate. For example, the target analyte can come into direct contact with the collection substrate using, for example, a wiping, dabbing, or swabbing motion of the collection substrate on the solid or fluid surface. Additionally, the target analyte can be collected on a porous or fibrous collection substrate by passing a fluid (such as a liquid or a gas medium) through the substrate rather than simply contacting a surface of a solid or a fluid. Additionally, other factors including, for example, pressure, heat, air flow, water flow, electric fields, magnetism, light, or acoustic energy can be used to improve collection efficiency. For example, an electric field can be used to direct a charged target analyte from the collection substrate to an optical substrate for subsequent analysis. Furthermore, the electric field can then be used to remove the target analyte from the optical substrate.

As shown in FIG. 1, an example embodiment of a collection substrate 10 is retained to a facilitating housing 12, which provides mechanical support for the collection substrate 10 made of a selected material and of a selectable geometry to optimally collect a target analyte. The housing 12 may be constructed of injection molded polypropylene and configured to provide structural retention and support for the collection substrate 10, such as by heat staking, ultrasonic welding, by use of an adhesive, or mechanical attachment, as examples. The collection substrate 10 may be a steel mesh or a glass fiber membrane with a high affinity for a target analyte. The collection substrate 10 shown in FIG. 1 includes a border portion 14 and a centered hub 16 that extends above the surface of the border portion 14. The centered hub 16 may be configured with dimensions to match substantially the surface area of an analysis component, such as an ATR crystal. That configuration enhances the likelihood that a target analyte will be concentrated on the hub 16 rather than dispersed across the entire surface area of the collection substrate 10. The collection substrate 10 may be formed by any means suitable to establish sufficient structural integrity as a function of the material selected to make the collection substrate 10. It may also be formed to enable an effective interface with a spectrometer. Other dimensions and geometries may be used to maximize capture of the target analyte to the collection substrate 10 and so the configuration of the collection substrate of the present invention is not limited to that which is shown in FIG. 1.

The housing 12 is shown in FIG. 1 as a donut arrangement with a primary structural body 20 spacing a first retaining ring 22 from a second retaining ring 24. This particular arrangement is suitable for facilitating the interface of the collection substrate 10 with the target analyte. Specifically, a suitable wand or arm may be releasably secured to the housing 12 by frictionally fitting or snapping it to the structural body 20 between the first ring 22 and second ring 24. Of course, other housing configurations of any size or shape necessary to collect the target analyte from the sampling medium may be used, including for suitable connection to any sort of device that may be employed to enable physical contact between the collection substrate 10 and the target analyte. The housing may contain one or multiple collection substrates, which can be used singly or cooperatively. The housing may be further connected to a handle of adjustable length and angle to facilitate analyte collection from a variety of surface geometries. The housing may also include a subsystem that allows for efficient identification or tracking, for example including RFID or GPS hardware.

Materials selected for the collection substrate control the capture of the target analyte from a sample. For example, the substrate can be formed entirely or in part of a material with an affinity for the target analyte. The types of collection substrate materials include but are not limited to stainless steel, metals of any kind, metal oxides, glass, Teflon, polypropylene, polyethylene, or polymers of any kind. The collection substrate material may be a mesh, membrane, fiber, porous, or nonporous in nature. Additionally, a coating can be added to the substrate to increase the substrate's affinity for a target analyte. In one particular embodiment, a glass fiber membrane can be surface treated with methyl groups to render it more hydrophobic. Alternatively, reagents or other materials can be added to the target analyte or substrate(s) at any time during the analytical process that will help control the transfer of the target analyte or facilitate analysis of the substrate. In one particular embodiment, a membrane can have nanoparticles with high affinity for a target analyte. In another particular embodiment, silver or gold nanoparticles can be included in the porous network of the membrane to allow for a surface enhancement when analyzed using Raman spectroscopy.

Figure 2:
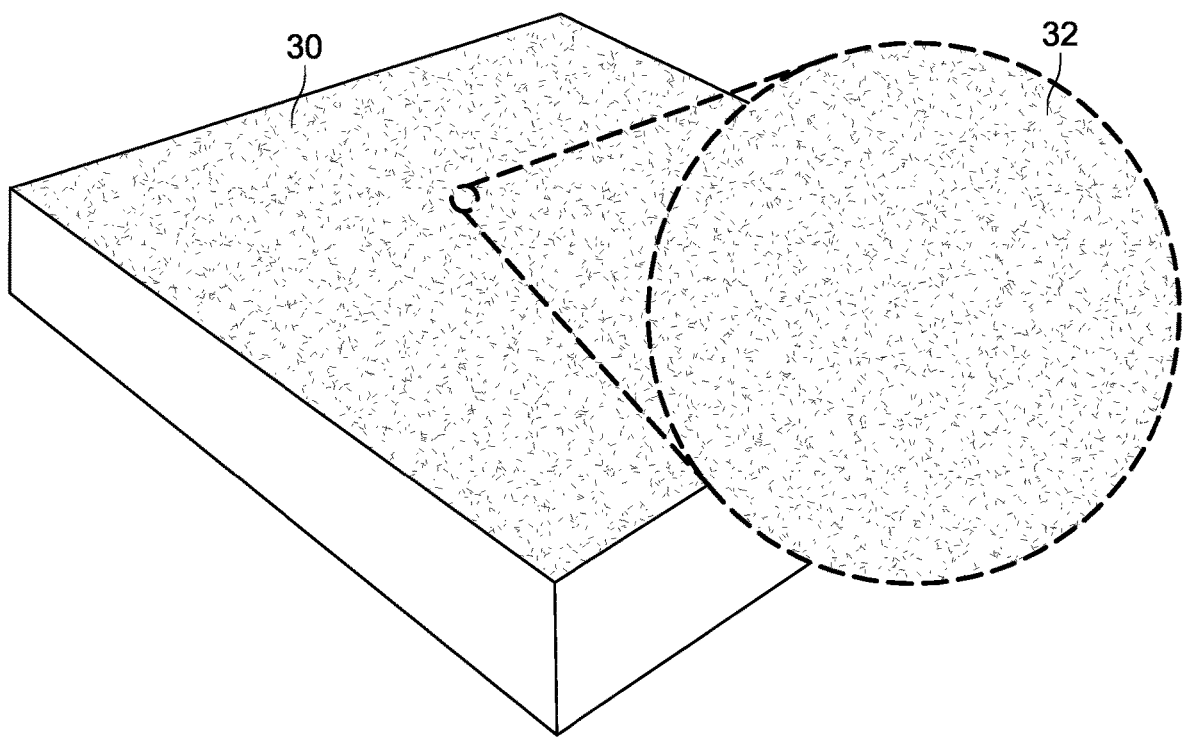
FIG. 2 is a close-up perspective view showing a target analyte that has been immobilized onto the capture region of the collection substrate of FIG. 1.

Once the target analyte is collected onto and/or into the collection substrate, the target analyte can be optimally prepared for analysis and analyzed using one of two general schemes. The first general scheme represented in FIG. 2, uses a collection substrate 30 alone as the target analyte retainer inserted into a spectroscopy tool for direct analysis of the target analyte. The collection substrate 30 of the first general scheme includes at least that portion of a collection substrate containing a target analyte 32 but which may include the entirety of the collection substrate, such as either or both of the hub 16 and the border 14 and hub 16 of the collection substrate 10 of FIG. 1. In the case of the first general scheme, the collection substrate 30 is also the optical substrate. In order for this to occur, the substrate 30 must not compromise the capability of the optical spectroscopy technique being used for analysis. In one particular embodiment (see example 1), a polyethylene membrane embodiment of the collection substrate 30 that has collected silver cyanide from a surface can be analyzed using IR spectroscopy because the bands due to the polyethylene membrane do not interfere with the band due to silver cyanide at 2169 cm$^{-1}$. The polyethylene membrane can be analyzed in transmission mode if the collection substrate 30 does not completely obstruct the IR beam. Alternatively, the polyethylene membrane can be analyzed using ATR infrared spectroscopy.

Figure 3:
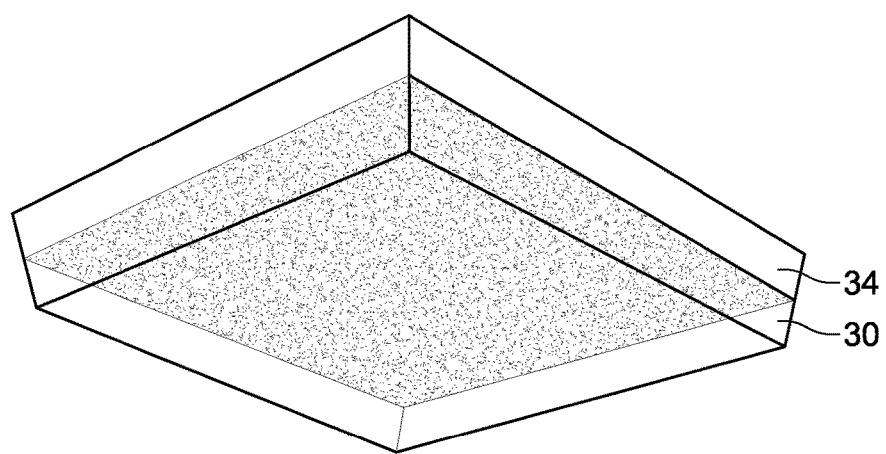
FIG. 3 is a perspective view showing the capture region of the collection substrate of FIG. 2 with target analyte applied to an ATR crystal of an ATR IR spectrometer for optical analysis.

If the collection substrate 30 is to be used for direct analysis by transmission spectroscopy, the material of the substrate 30 must be sufficiently transparent in the spectral region of interest and the target analyte 32 must be immobilized in such a manner that optical scattering does not obscure the measurement. For example, materials such as polymers, metal oxides, as well as common IR window materials, may be used as the collection substrate 30 in that type of analysis. Alternatively, the collection substrate 30 may be formed of other materials suitable for analysis using ATR infrared spectroscopy including polymers (including, but not limited to, polyethylene, polycarbonate, nylon, Teflon, polypropylene, polyethersulfone, and metalized variants of each), fibrous materials (including, but not limited to, cellulose, cotton, glass wool, stainless steel wool, quartz wool, Teflon wool, and other textiles), or commonly used membranes or filters. Other materials and configurations may be used as the collection substrate 30 when other spectroscopy tools and methods are employed, provided such materials and/or configurations do not obscure measurement. FIG. 3 shows an example of the collection substrate 30 with the target analyte 32 captured thereto pressed on to an ATR crystal 34 for the purpose of carrying out ATR IR spectroscopy.

Figure 4:
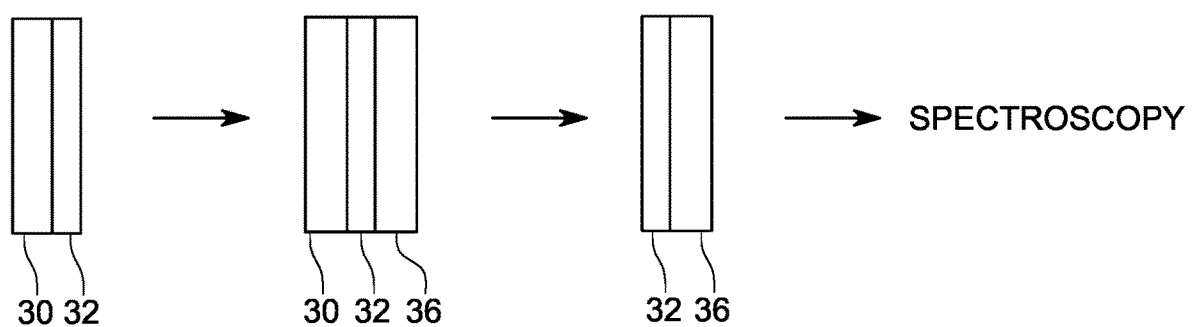
FIG. 4 is a schematic representation showing how a target analyte is collected onto a collection substrate and is transferred to an optical substrate to enable analysis by optical spectroscopy

The second general scheme represented simply in FIG. 4, to analyze the target analyte involves the transfer of the target analyte from the collection substrate 30 to a support substrate 36 that facilitates spectroscopy, referred to herein as an optical substrate 34 when the spectrometer is an optical one, but is not limited to solely an optical support. For transmission infrared spectroscopy, the optical substrate 36 can be formed of common IR window materials, (for example, silicon, zinc selenide, KRS-5, germanium, diamond), materials transparent in the infrared region of interest or engineered in such a way that it is at least in part transparent (for example, polyethylene, stainless steel wool, polycarbonate, nylon, Teflon, or polypropylene), or any other suitable material that does not contain bands in the infrared region that make analysis of the target analyte impossible. For ATR infrared spectroscopy, the optical substrate 36 can be formed of commercially available ATR crystal material (for example silicon, zinc selenide, KRS-5, germanium, diamond). For reflection infrared spectroscopy, any material that reflects an infrared beam can be used for the optical substrate 36, for example, a gold or silver coated glass slide or a metalized polymer. For Raman spectroscopy, any suitable material can be used for the optical substrate 36 as long as the substrate does not contain bands or fluoresce in such a way that analysis of the target analyte is impossible.

Other materials can be added to the optical substrate 36 or collection substrate 30 to control the transfer of the target analyte 32 from the collection substrate 30 to the optical substrate 36. For example, when the substrate 36 is an optical one, the optical substrate 36 can be formed entirely or in part of a material with a higher affinity for the target analyte 32 than the collection substrate 30. Additionally, the collection substrate 30 can include a coating that facilitates transfer of the target analyte 32 to the optical substrate 36. Additionally, a coating can be added to the optical substrate 36 to increase the optical substrate's affinity for a target analyte, thus facilitating transfer of the target analyte 32. Alternatively, reagents or other materials can be added to the target analyte 32 or optical substrate 36 at any time during the analytical process that will enhance the transfer of the target analyte 32 to the optical substrate 36. Any acceptable method can be used to transfer the target analyte 32 from the collection substrate 30 to the optical substrate 36. Factors including pressure, heat, air flow, water flow, electric fields, magnetism, light, or acoustic energy can also be used to improve transfer efficiency from the collection substrate 30 to the optical substrate 36. In one particular embodiment, a diamond ATR crystal is used as the optical substrate 36 in conjunction with a polyethylene collection substrate 30 used to measure the toxic substance silver cyanide.

The process of capturing the analyte to one or more collection substrates may also include a process to dry the substrate(s). This process may be required when there may be a concern that the fluid medium interferes with analysis by a particular spectroscopic technique. For example, water is highly absorbing in the infrared region, thus complicating analysis by most modes of infrared spectroscopy. Any suitable method that does not compromise analysis or combination of methods for removing a fluid medium can be used, including for example vacuum, compressed gas, or heat. Additionally, the use of a chemical fluid displacement agent may be effective for instances where another fluid is appropriate for direct analysis by the preferred mode of spectroscopy.

The process of detecting the captured analyte also includes the use of a spectrometer, such as an optical spectrometer producing an optical beam that passes through or reflects off the particles and sometimes the substrate. The change in the optical signature of the optical substrate allows the spectrometer to detect and measure the target analyte. Examples of suitable spectroscopic detection arrangements are described as follows.

Any optical spectroscopic technique can be used as part of the detection process, such as any of those known in the art. In brief, IR spectroscopy is the absorption measurement of different IR frequencies by a sample positioned in the path of an IR beam. The main goal of IR spectroscopic analysis is to determine the chemical functional groups found in the sample. Different functional groups absorb characteristic frequencies of IR radiation. IR spectra are obtained by detecting changes in transmittance or absorption intensity as a function of frequency.

UV or visible spectroscopy is the absorption measurement of different UV or visible wavelengths of light by a sample positioned in the path of a UV or visible beam. UV or visible spectroscopy measures the light change by a sample due to an electronic transition in the probed material. Some UV or visible spectrometers are compact, low power and can be transported where needed. Such spectrometers may be used for the detection of analytes captured with the collection substrate of the present invention.

Specular reflectance is a mode of IR, UV, or visible spectroscopy that involves a mirror-like reflection off of the front surface of the particle and varies with absorption index of the material in a manner that is different than transmission or diffuse reflectance. Such spectroscopy may be used for the detection of analytes captured with the collection substrate of the present invention.

In diffuse reflection infrared Fourier transform (DRIFT) spectroscopy, the reflection of incident radiation off of the particle occurs at many angles rather than just one angle as is the case for specular reflection. Such spectroscopy is used when the material being interrogated is a rough surface or highly scattering particles and may be used for the detection of analytes captured with the collection substrate of the present invention.

In photoacoustic spectroscopy (PAS) the modulated IR radiation from an FTIR interferometer is focused on a sample placed inside a chamber which typically contains an IR-transparent gas. IR radiation absorbed by the sample converts into heat inside the sample. The heat diffuses to the sample surface then into the surrounding gas atmosphere and causes expansion of a boundary layer of gas next to the sample surface. Thus, the modulated IR radiation produces intermittent thermal expansion of the boundary layer and generates pressure waves which are detected by a microphone or piezoelectric sensor. Such spectroscopy may be used for the detection of analytes captured with the collection substrate of the present invention.

Emission infrared spectroscopy is another technique in which the sample is heated to an elevated temperature, emitting enough energy in the infrared region to be detected by an FTIR detector. Emission spectral bands occur at the same frequencies as absorption bands. Such spectroscopy may be used for the detection of analytes captured with the collection substrate of the present invention.

Ion mobility and mass spectroscopy are also other detection tools that may be employed to detect analytes captured with the collection substrate of the present invention.

As earlier noted, ATR is another mode of IR spectroscopy in which the sample is placed on the surface of a dense, high refractive index crystal. The IR beam is directed onto the beveled edge of the ATR crystal and is totally internally reflected through the crystal with single or multiple reflections. The beam penetrates a very short distance into the sample on the surface before the complete reflection occurs. This penetration is called the evanescent wave and typically is at a depth of a few micrometers for infrared radiation. Its intensity is reduced (attenuated) by the sample in regions of the IR spectrum where the sample absorbs. Such spectroscopy may be used for the detection of analytes captured with the collection substrate of the present invention.

Fluorescence spectroscopy measures the emission of light after a sample has absorbed light of a different frequency. Fluorescence is typically used in the UV or visible region of the electromagnetic spectrum, but other types of fluorescence (e.g., X-Ray) can also be used for some applications. Fluorescence instruments for the UV and visible regions of the electromagnetic spectrum can be compact, low power and transportable where needed. Such spectroscopy may be used for the detection of analytes captured with the collection substrate of the present invention.

Raman spectroscopy is a technique that measures a characteristic shift from a laser source caused by inelastic light scattering of a sample. Raman spectroscopy gives functional group information complimentary to FTIR, but has advantages to FTIR in some cases, one of which is that water present in the sample does not interfere with analysis by Raman. Such spectroscopy may be used for the detection of analytes captured with the collection substrate of the present invention.

EXAMPLES

Example 1: Silver Cyanide Detection in an Aqueous Residue on a Solid Surface Using Transmission and ATR Infrared Spectroscopy In this example, an aqueous residue containing toxic silver cyanide was collected onto the collection substrate of the present invention and analyzed in 3 different ways using infrared spectroscopy to demonstrate several embodiments of the invention. The collection substrate was acquired from Orono Spectral Solutions, Inc. (OSS) of Bangor, Me. As used herein, "cyanide" refers to any chemical compound including a carbon atom triple-bonded to a nitrogen atom. It may be referred to herein from time to time as "CN." Silver cyanide may be referred to herein as AgCN.

Preparation of the AgCN Residue

AgCN residue was prepared by dissolving 100 mg of silver nitrate into 1 mL of deionized water. Once dissolved, 25 mg of sodium cyanide was added to the solution, which then turned cloudy as silver cyanide particles were formed. This slurry was then poured onto a laboratory bench, to simulate an aqueous residue.

Collection of AgCN Residue Using OSS Collection Substrate

The residue was collected using OSS Collection Substrate commercially available from OSS as part number PN 092385 and a wiping motion to collect the residue. For this example, two collection substrates were used to demonstrate multiple embodiments. One of the OSS Collection Substrates was dried using compressed air and analyzed using transmission FTIR Spectroscopy.

Transmission FTIR Spectroscopy of OSS Collection Substrate

Figure 5:
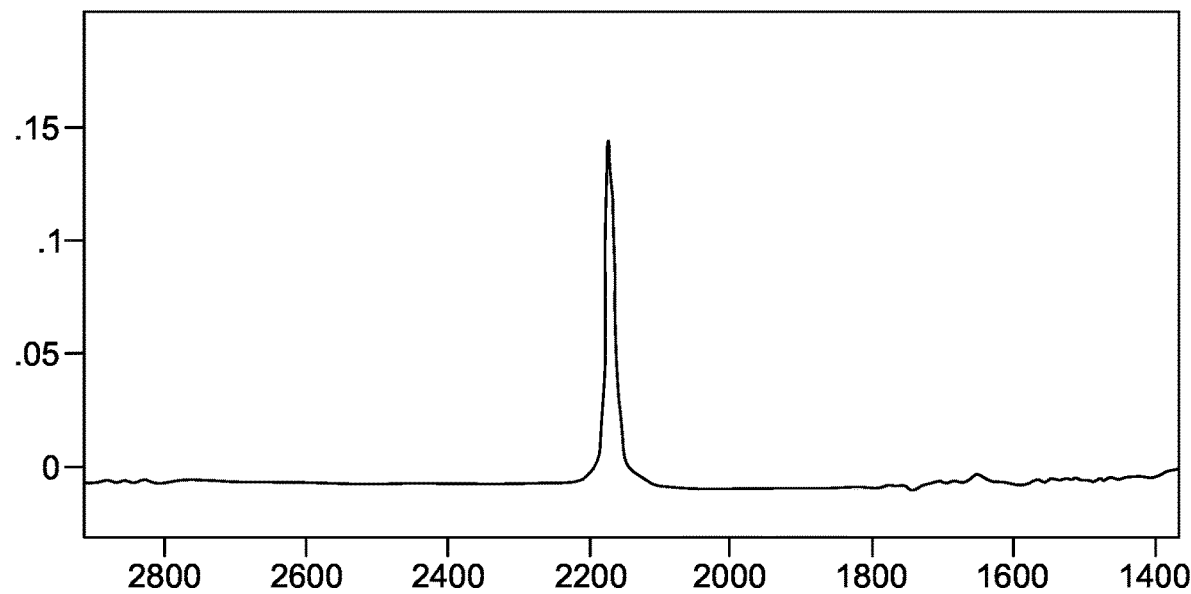
FIG. 5 is a graphical representation of an IR spectrum obtained with transmission IR spectroscopy for silver cyanide residue captured with the collection substrate of the present invention.

Transmission FTIR spectroscopy (using an ABB-Bomem MB3000 spectrometer) was used to detect cyanide collected onto the OSS Collection Substrate. The spectrum shown in FIG. 5 illustrates an absorbance spectrum using an unexposed OSS Collection Substrate as a reference. The peak near 2169 cm is assigned to the CN stretching mode in AgCN. In this example, the bands due to the OSS Collection Substrate do not interfere with CN analysis, so transmission FTIR spectroscopy is an appropriate mode of spectroscopy for this application.

ATR FTIR Spectroscopy of OSS Collection Substrate

Figure 6:
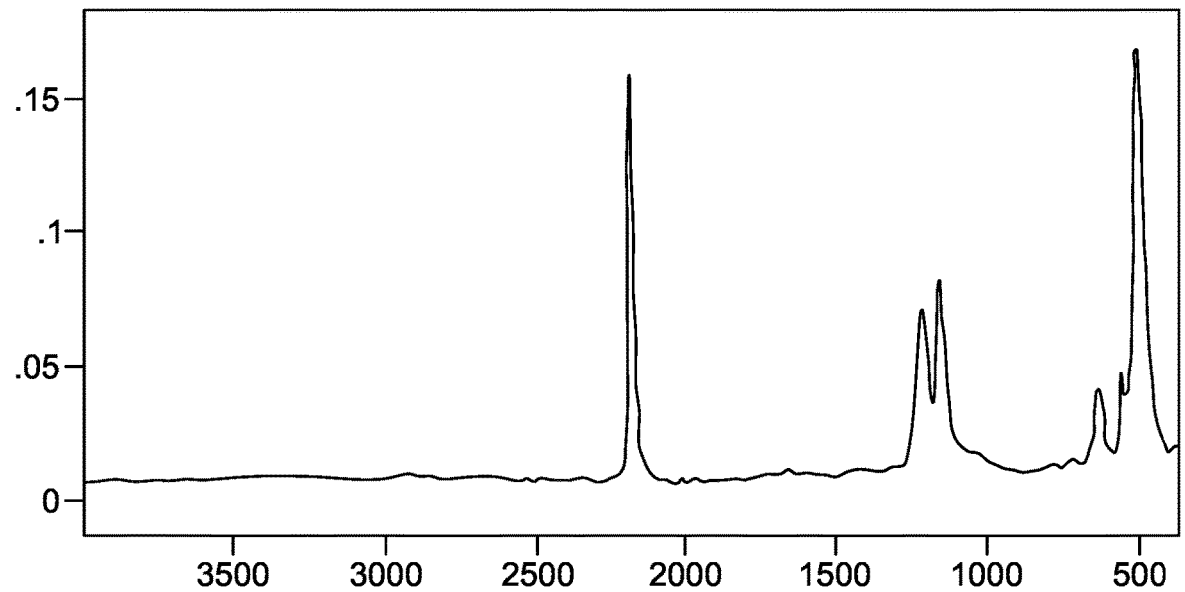
FIG. 6 is a graphical representation of an IR spectrum obtained with ATR IR spectroscopy for silver cyanide residue captured with the collection substrate of the present invention.

ATR FTIR spectroscopy (using a Bruker Alpha spectrometer outfitted with a Bruker Platinum ATR accessory) was used to measure AgCN collected on the OSS Collection Substrate. FIG. 6 illustrates an absorbance spectrum using the diamond ATR crystal as a reference. The peak near 2169 $cm^1$ is assigned to the CN stretching mode in AgCN. In this example, the bands due to the OSS Collection Substrate do not interfere with CN analysis, so ATR FTIR spectroscopy is an appropriate mode of spectroscopy for this application.

Figure 7:
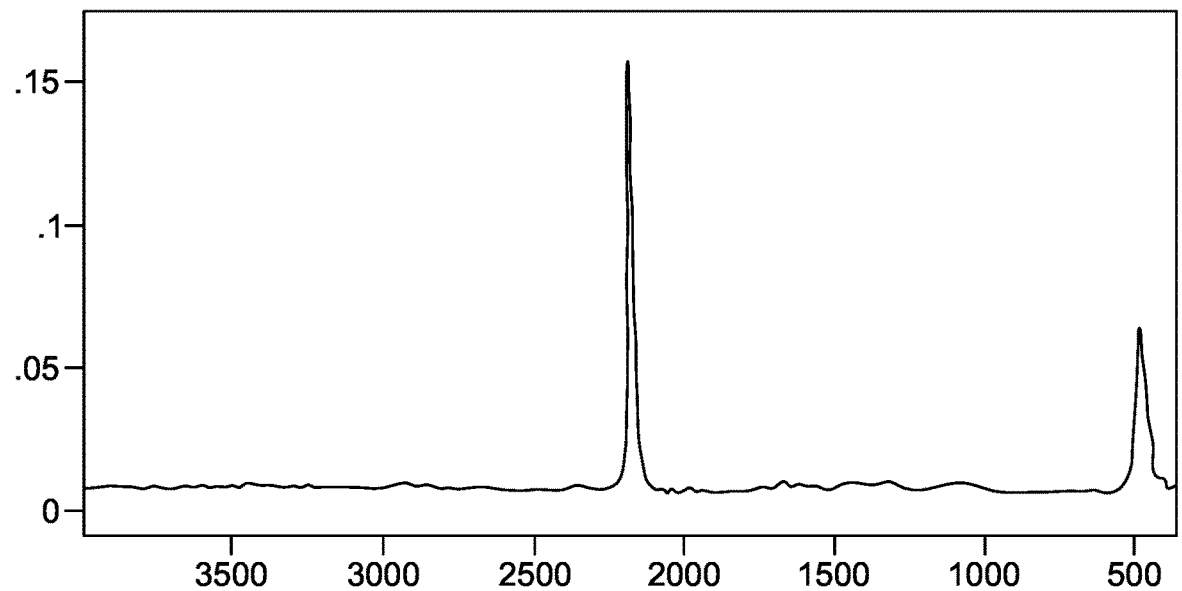
FIG. 7 is a graphical representation of an IR spectrum obtained with ATR IR spectroscopy for silver cyanide residue after transfer from the collection substrate of the present invention to a diamond ATR crystal.

ATR FTIR Spectroscopy of AgCN Transferred from OSS Collection Substrate to the Optical Substrate ATR FTIR spectroscopy (using a Bruker Alpha spectrometer outfitted with a Bruker Platinum ATR accessory) was used to measure AgCN that was transferred from the OSS Collection Substrate to an optical substrate. FIG. 7 is an absorbance spectrum using the diamond ATR crystal as a reference. The peak near 2169 $cm^1$ is assigned to the CN stretching mode in AgCN. In this example, bands due to the OSS Collection Substrate are not present because AgCN was transferred from the OSS Collection Substrate to the ATR crystal, which served as the optical substrate.

Evaluation of AgCN Transfer from OSS Collection Substrate to the Optical Substrate The percent of AgCN transferred from the OSS Collection Substrate to the optical substrate is calculated by taking the ratio of the AgCN peak measured on the OSS Collection Substrate (0.1514—FIG. 6) and on the optical substrate (0.1506—FIG. 7). This indicates that over 99% of AgCN was transferred from the OSS Collection Substrate to the optical substrate.

Example 2: Silver Phosphate Detection in an Aqueous Residue on a Solid Surface Using ATR Infrared Spectroscopy In this example, an aqueous residue containing silver phosphate was collected onto the collection substrate of the present invention and analyzed in two different ways using infrared spectroscopy to demonstrate several embodiments of the invention. The collection substrate was acquired from OSS.

Preparation of the Silver Phosphate Residue

Silver phosphate residue was prepared by dissolving 200 mg of silver nitrate into 1 mL of deionized water. Once dissolved, 25 mg of sodium cyanide was added to the solution, which then turned cloudy as silver phosphate particles were formed. This slurry was then poured onto a laboratory bench, to generate an aqueous residue.

Collection of Silver Phosphate Residue Using OSS Collection Substrate

The residue was collected using OSS Collection Substrate (PN 092385) and a wiping motion to collect the residue. For this example, two collection substrates were used to demonstrate multiple embodiments. One of the OSS Collection Substrates was dried using compressed air and analyzed using transmission FTIR Spectroscopy.

ATR FTIR Spectroscopy of OSS Collection Substrate

Figure 8:
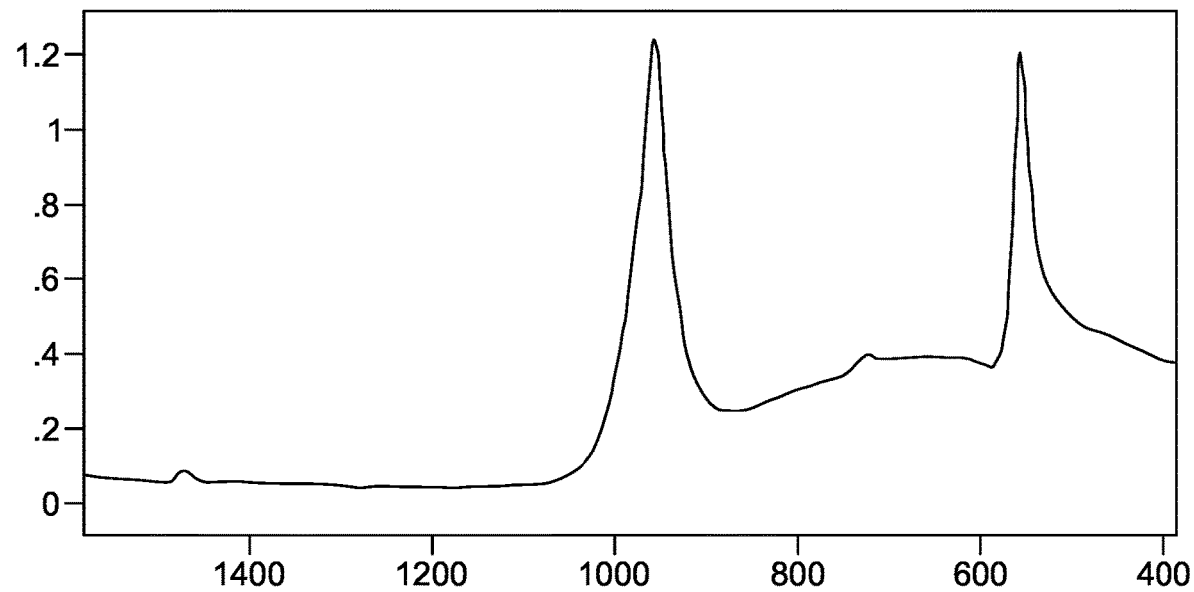
FIG. 8 is a graphical representation of an IR spectrum obtained with ATR IR spectroscopy for silver phosphate residue captured with the collection substrate of the present invention.

ATR FTIR spectroscopy (using a Bruker Alpha spectrometer outfitted with a Bruker Platinum ATR accessory) was used to measure silver phosphate collected on the OSS Collection Substrate. FIG. 8 illustrates an absorbance spectrum using the diamond ATR crystal as a reference. The peak near 960 $cm^{-1}$ is assigned to silver phosphate. In this example, the bands near 1460 $cm^{-1}$ due to the OSS Collection Substrate do not interfere with phosphate analysis, so ATR FTIR spectroscopy is an appropriate mode of spectroscopy for this application.

Figure 9:
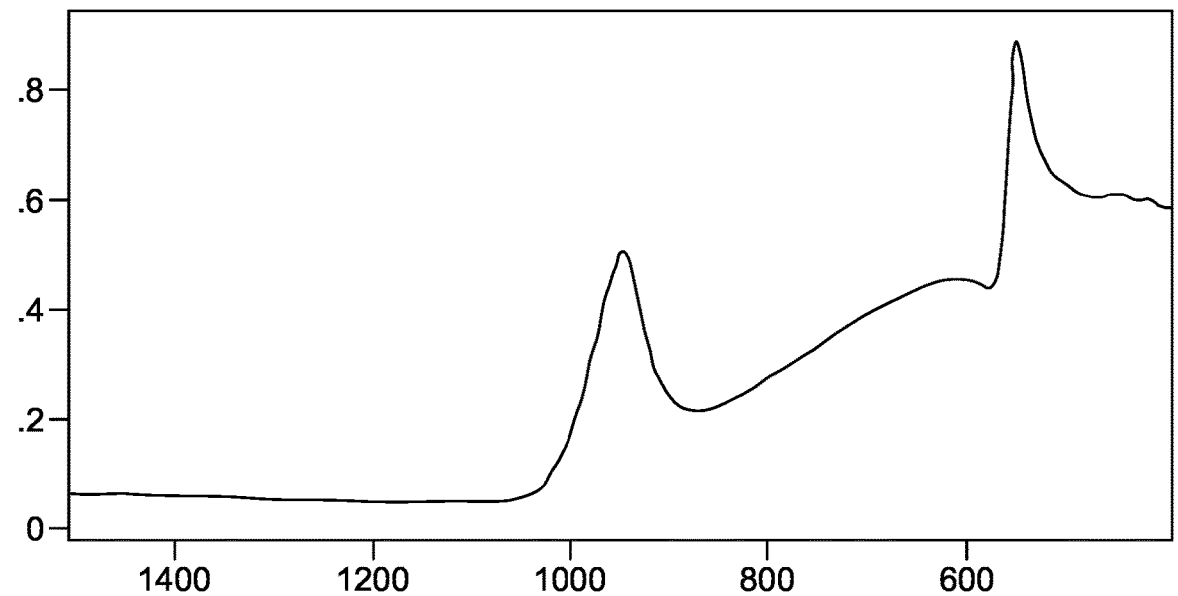
FIG. 9 is a graphical representation of an IR spectrum obtained with ATR IR spectroscopy for silver phosphate residue after transfer from the collection substrate of the present invention to a diamond ATR crystal.

ATR FTIR Spectroscopy of Silver Phosphate Transferred from OSS Collection Substrate to the Optical Substrate ATR FTIR spectroscopy (using a Bruker Alpha spectrometer outfitted with a Bruker Platinum ATR accessory) was used to measure silver phosphate that was transferred from the OSS Collection Substrate to the optical substrate. FIG. 9 illustrates an absorbance spectrum using the diamond ATR crystal as a reference. The peak near 960 $cm^{-1}$ is assigned to silver phosphate. In this example, bands due to the OSS Collection Substrate near 1460 $cm^{-1}$ are not present because silver phosphate was transferred from the OSS Collection Substrate to the ATR crystal, which serves as the optical substrate.

Evaluation of Silver Phosphate Transfer from OSS Collection Substrate to the Optical Substrate The percent of silver phosphate transferred from the OSS Collection Substrate to the optical substrate is calculated by taking the ratio of the silver phosphate peak measured on the OSS Collection Substrate (1.06—FIG. 8) and the optical substrate (0.35—FIG. 9). This indicates that 33% of silver phosphate was transferred from the OSS Collection Substrate to the optical substrate. This percentage of transfer from the OSS Collection Substrate to the optical substrate was higher than all other collection substrates that were tested: Teflon (0.4% transfer), nylon (1.1%), and vinyl (<0.1%).

Example 3: Detection of Residue Containing BG Spores on Surfaces

In this example, a residue containing *Bacillus globigii* spores (BG) was collected onto the collection substrate of the present invention and analyzed using ATR infrared spectroscopy. The collection substrate was acquired from OSS.

Preparation of the BG Spore Residue

BG spore residue was prepared by applying a fine powder of BG spores on a steel surface.

Collection of BG Spore Residue Using OSS Collection Substrate

The residue was collected using OSS Collection Substrate (PN 04031982) and a wiping motion to collect the residue.

ATR FTIR Spectroscopy of OSS Collection Substrate

Figure 10:
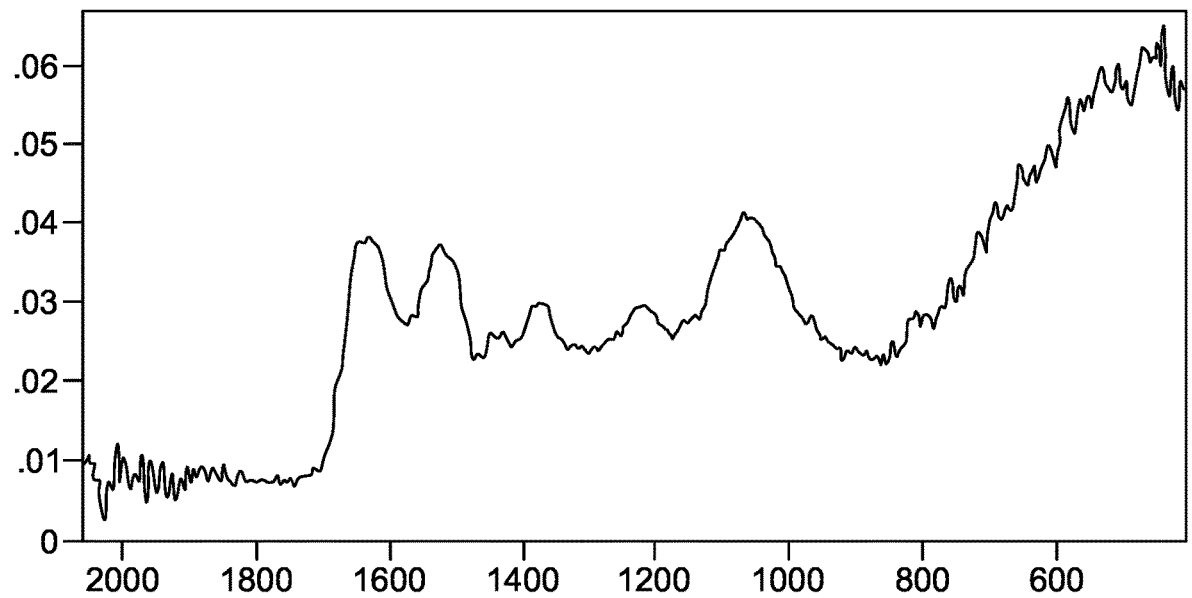
FIG. 10 is a graphical representation of an IR spectrum obtained with ATR FTIR spectroscopy for BG spore captured with the collection substrate of the present invention.

ATR FTIR spectroscopy (using a Bruker Alpha spectrometer outfitted with a Bruker Platinum ATR accessory) was used to measure BG spore residue collected on the OSS Collection Substrate (FIG. 10). The peaks near 1640 and 1560 $cm^{-1}$ are due to amide bands from protein material in the spore. The peak near 1100 $cm^{-1}$ is due to polysaccharide bands from material in the spore. In this example, bands near 1460 $cm^{-1}$ do not interfere with FTIR analysis of the key bands due to spores, so the spores can be directly analyzed on the OSS Collection Substrate.

Example 4: Silver Cyanide Detection in an Aqueous Residue on a Solid Surface Using Raman Spectroscopy In this example, an aqueous residue containing toxic AgCN was collected onto the collection substrate of the present invention and analyzed using a hand-held Raman spectrometer. The collection substrate was acquired from OSS.

Preparation of the AgCN Residue

AgCN residue was prepared by dissolving 100 mg of silver nitrate into 1 mL of deionized water. Once dissolved, 25 mg of sodium cyanide was added to the solution, which then turned cloudy as silver cyanide particles were formed. This slurry was then poured onto a laboratory bench, to simulate an aqueous residue.

Collection of AgCN Residue Using OSS Collection Substrate

The residue was collected using OSS Collection Substrate (PN 092385) and a wiping motion to collect the residue.

Raman Spectroscopy of OSS Collection Substrate

Figure 11:
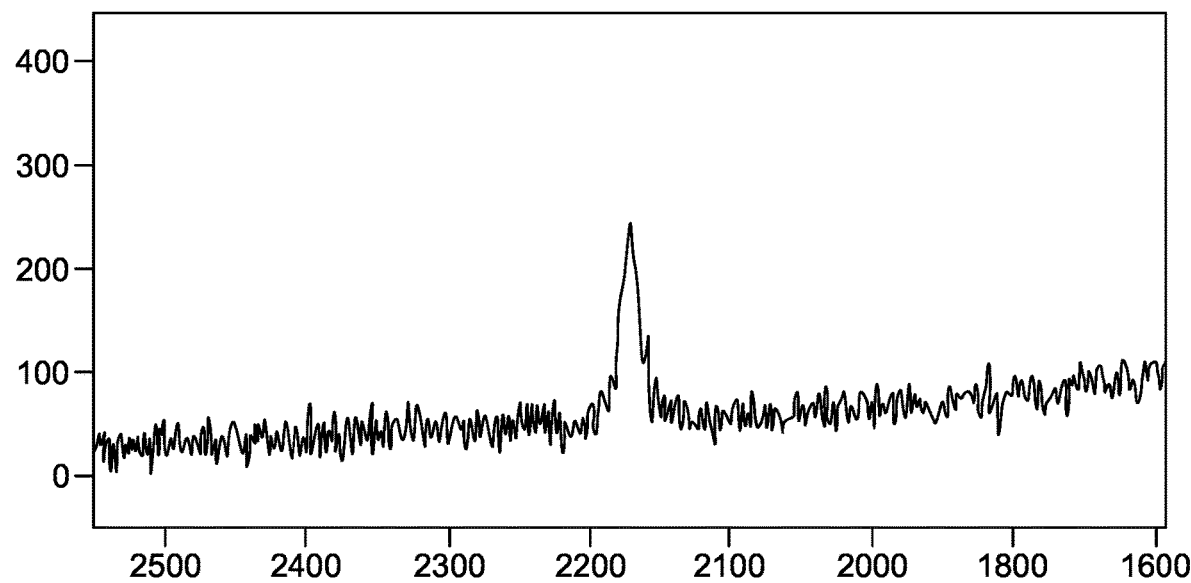
FIG. 11 is a graphical representation of a Raman spectrum obtained with Raman spectroscopy for silver phosphate residue captured with the collection substrate of the present invention.

Raman spectroscopy, using a Thermoscientific AhuraFD handheld Raman spectrometer, was used to detect cyanide collected onto the OSS Collection Substrate. The spectrum shown in FIG. 11 is an absorbance spectrum using an unexposed OSS Collection Substrate as a reference. The peak near 2169 cm is assigned to the CN stretching mode in AgCN. In this example, the bands due to the OSS Collection Substrate do not interfere with CN analysis, so direct Raman analysis of the OSS Collection Substrate is acceptable.

Example 5: Silicone Oil Residue Detection on a Solid Surface Using ATR Infrared Spectroscopy In this example, a silicone oil residue was collected onto the collection substrate of the present invention and analyzed in 2 different ways using infrared spectroscopy to demonstrate several embodiments of the invention. The collection substrate was acquired from OSS.

Preparation of the Silicone Oil Residue

Silicone oil residue was prepared by spraying a fine mist of silicone lubricating spray onto a steel substrate.

Collection of Silicone Oil Residue Using OSS Collection Substrate

The residue was collected using OSS Collection Substrate (PN 040382) and a wiping motion to collect the residue. For this example, two collection substrates were used to demonstrate multiple embodiments.

ATR FTIR Spectroscopy of OSS Collection Substrate

Figure 12:
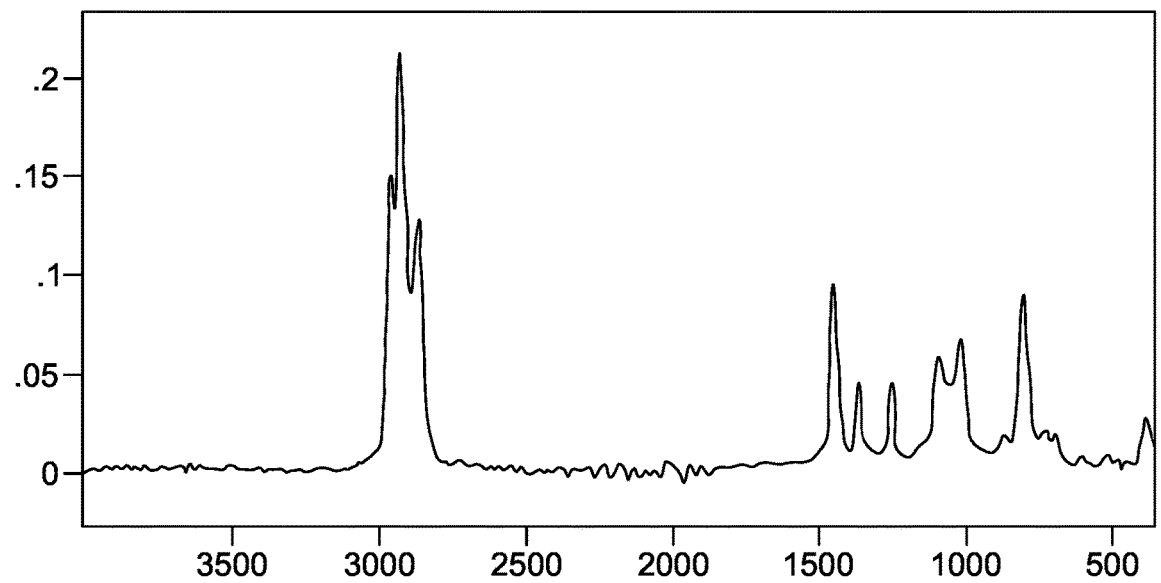
FIG. 12 is a graphical representation of an IR spectrum obtained with ATR IR spectroscopy for silicone oil residue after transfer from the collection substrate of the present invention to a diamond ATR crystal.

ATR FTIR spectroscopy (using a Bruker Alpha spectrometer outfitted with a Bruker Platinum ATR accessory) was used to measure silicone oil collected on the OSS Collection Substrate. FIG. 12 shows an absorbance spectrum of the silicone oil residue on the OSS Collection Substrate using the diamond ATR crystal as a reference. The double peak centered around 1056 cm is characteristic of the Si—O—Si backbone of silicone oil. The bands between 3000 $cm^{-1}$ and 2800 $cm^{-1}$ are due to C—H stretching modes found in silicone oil. In this example, the bands near 1460 $cm^{-1}$ due to the OSS Collection Substrate do not interfere with silicone oil analysis, so ATR FTIR spectroscopy is an appropriate mode of spectroscopy for this application.

Evaluation of Silicone Oil Transfer from OSS Collection Substrate to the Optical Substrate The percent of silicone oil transferred from the OSS Collection Substrate to the optical substrate is calculated by taking the ratio of the 1016 $cm^{-1}$ peak heights measured on the OSS Collection Substrate (0.055) and the optical substrate (0.035). This indicates that 64% of silicone oil was transferred from the OSS Collection Substrate to the Optical Substrate. This percentage of transfer from the OSS Collection Substrate to the optical substrate was markedly higher than all other collection substrates that were tested: Teflon (<0.1% transfer), polypropylene (2.3% transfer), polyethylene (1.4% transfer) and vinyl (1.2% transfer).

Example 6: Malathion Detection on a Solid Surface Using DRIFT Spectroscopy

In this example, a malathion oil residue was collected onto the collection substrate of the present invention and analyzed using DRIFT spectroscopy to demonstrate one embodiment of the invention. The collection substrate was acquired from OSS.

Preparation of the Malathion Residue

Malathion residue was prepared by spraying a fine mist of silicone lubricating spray onto a glass surface.

Collection of Malathion Residue Using OSS Collection Substrate

The residue was collected using OSS Collection Substrate (PN 040382) and a wiping motion to collect the residue.

DRIFT Spectroscopy of OSS Collection Substrate

Figure 13:
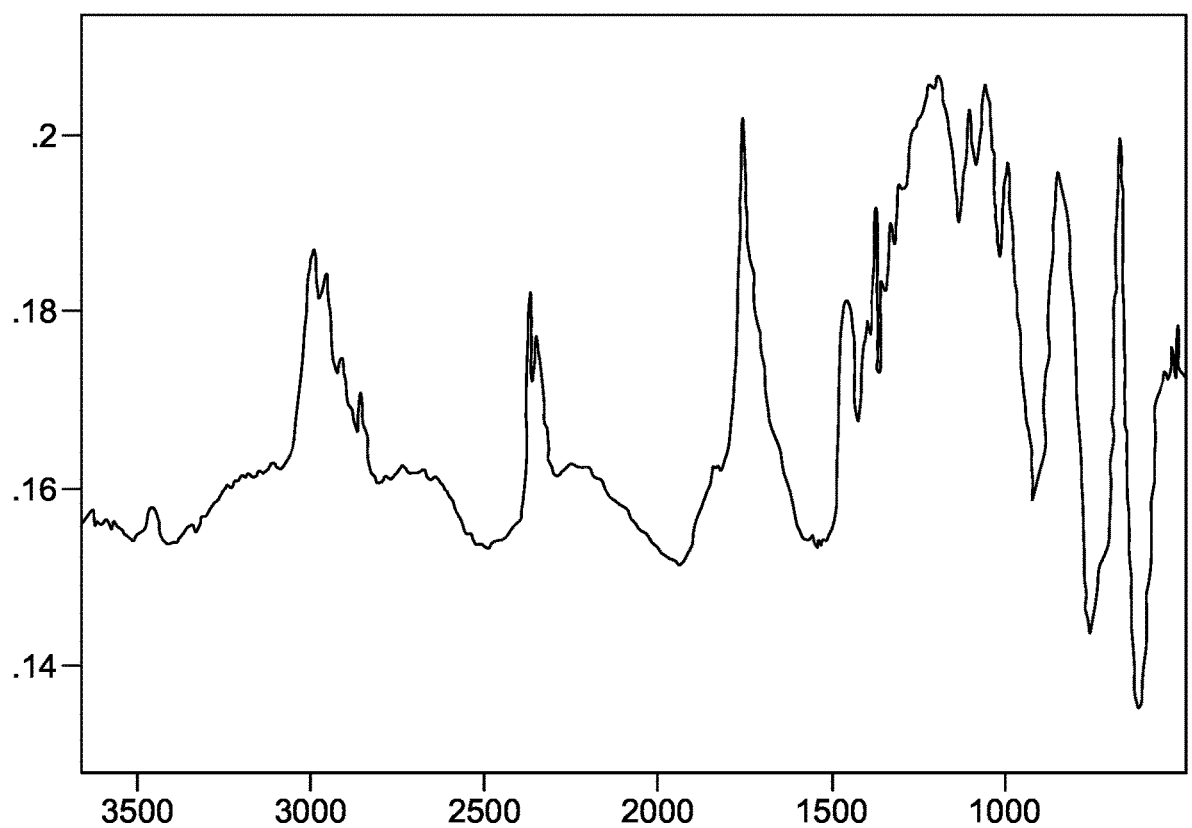
FIG. 13 is a graphical representation of an IR spectrum obtained with DRIFT spectroscopy for Malathion residue captured with the collection substrate of the present invention.

DRIFT spectroscopy (Using an ABB Bomem MB3000 FTIR Spectrometer with a Harrick DRIFT Accessory) was used to detect malathion on the OSS Collection Substrate. FIG. 13 shows the spectrum of malathion on the OSS Collection Substrate, referenced against a clean OSS Collection substrate.

Example 7: Metal Coated Polymer Membranes Versus Metal Mesh for Increased Detection Sensitivity In this example, a dry residue of caffeine powder was collected with a stainless steel metal mesh and with a silver metal coated Teflon membrane to highlight the sensitivity advantages of the metal coated membrane invention. To ensure optical throughput matching, both collection substrates were retained to a centered hub on a facilitating housing as described in earlier sections, where the centered hub was configured to substantially match the surface area of the ATR crystal employed by the FTIR analyzer.

Figure 14:
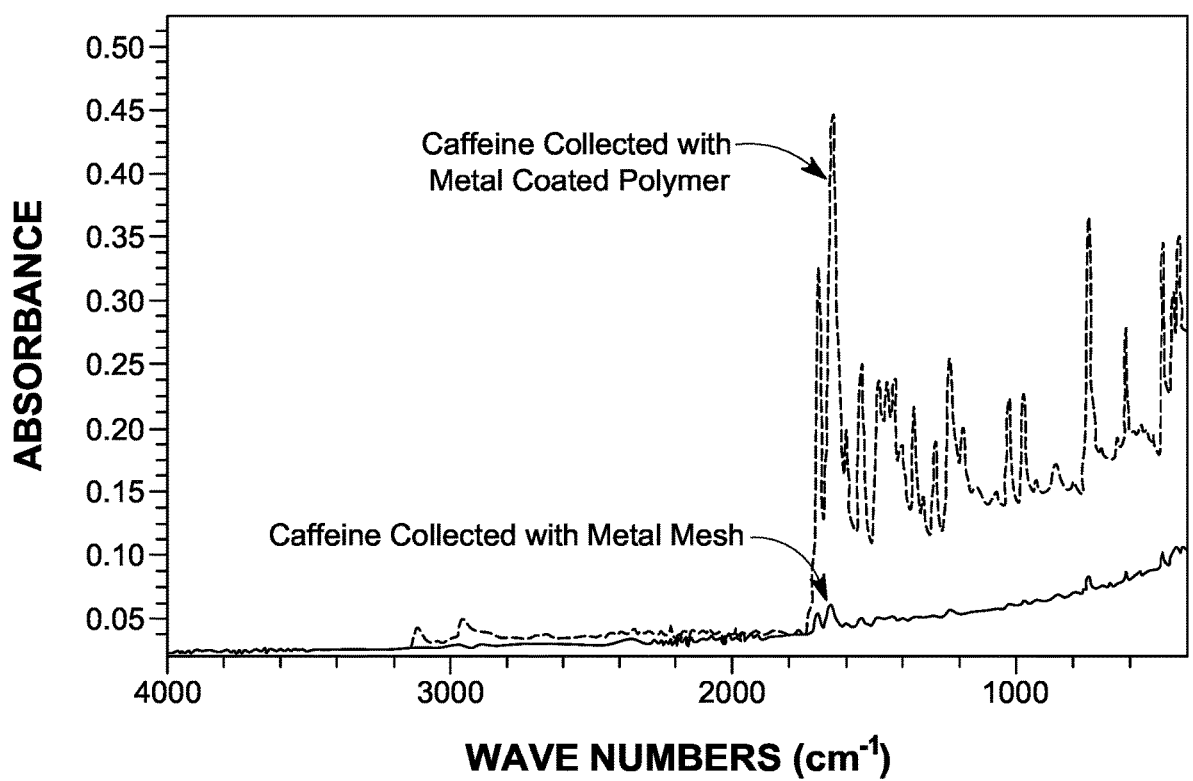
FIG. 14 is a graphical representation of an IR spectrum comparison obtained with ATR IR spectroscopy for caffeine powder captured on a metal mesh and on a metal-coated polymer membrane.

In this experiment, a known concentration of caffeine powder+methanol was prepared, where 10 µg of caffeine was pipetted from this solution and dispersed onto a round-bottom mortar to form a faint residue approximately 1 $cm^2$ in area once the methanol evaporated. Caffeine residues were prepared and sampled in this manner with both a stainless steel metal mesh and a metal coated Teflon sampling material. Visual inspection of the mortar before and after each experiment indicated that substantially all of the residue was collected in each experiment. Each sampling material was then analyzed using an ATR-FTIR spectrometer equipped with a single bounce diamond ATR crystal and anvil press. The results are shown in FIG. 14, where the metal coated polymer shows a significant enhancement in sensitivity over the metal mesh for the same amount of caffeine residue collected and analyzed. In both cases, no interfering signals are produced by the sampling materials since they are comprised of metal, where most metals are broadband absorbers in the mid-IR and do not contain distinct IR absorption bands.

Figure 15:
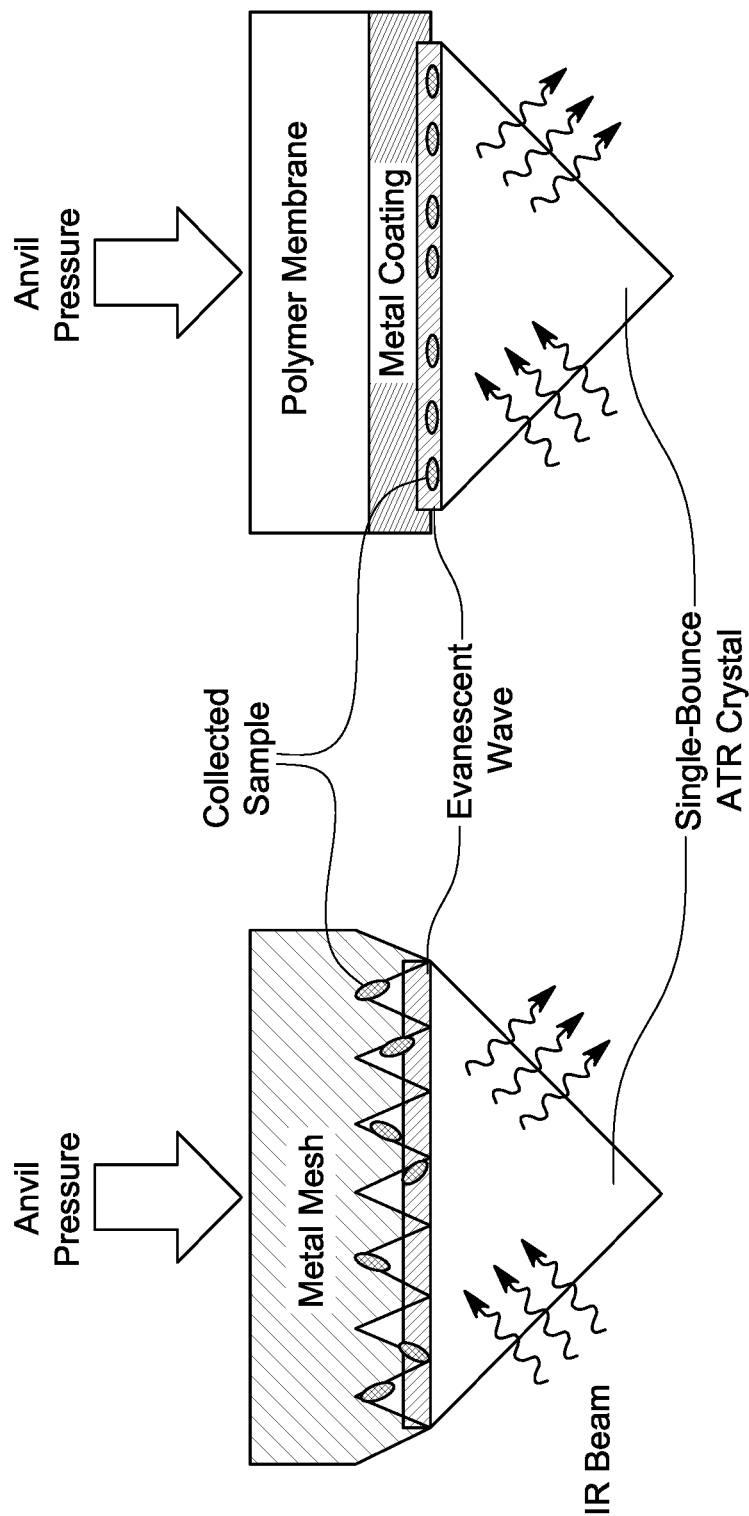
FIG. 15 is a simplified representation of the collection mechanisms for metal mesh and metal-coated polymer membrane substrates in relation to the representation of FIG. 14.

To explain the significant enhancement in the detection signal for the same amount of collected sample, the diagram in FIG. 15 illustrates the basic underlying concept behind the metal coated polymer invention. In the case of the stainless steel metal mesh, for small amounts of sample (e.g., 10 µg of a caffeine residue), much of the collected sample residues on parts of the metal mesh surface that are beyond the probe length of the IR evanescent wave due to the texture of the metal mesh material. In particular, the decay length of the evanescent probe wave extending from the ATR crystal surface is on the order of the IR wavelengths employed (e.g., 1-2 µm), whereas the woven metal mesh employed in this experiment contained strands that were larger than these dimensions, and thus created pockets that were beyond the reach of the IR probe beam. On the other hand, the compressibility of the polymer membrane base of the metal coated Teflon membrane allows for it to conform to the ATR crystal surface when pressures are applied (such as with a solid anvil press commonly employed with ATR-FTIR analyzers), thereby bringing all of the collected sample right up to the surface of the crystal and well within the probe length of the IR evanescent wave.

Example 8: Metal Coated Polymer Membranes Versus Polymer Membranes for Increased Detection Accuracy In this example, a dry residue of caffeine powder was collected with a Teflon membrane and with a silver metal coated Teflon membrane to highlight spectral accuracy advantages of the non-interfering metal coated membrane invention. To ensure optical throughput matching, both collection substrates were retained to a centered hub on a facilitating housing as described in earlier sections, where the centered hub was configured to substantially match the surface area of the ATR crystal employed by the FTIR analyzer.

Figure 16:
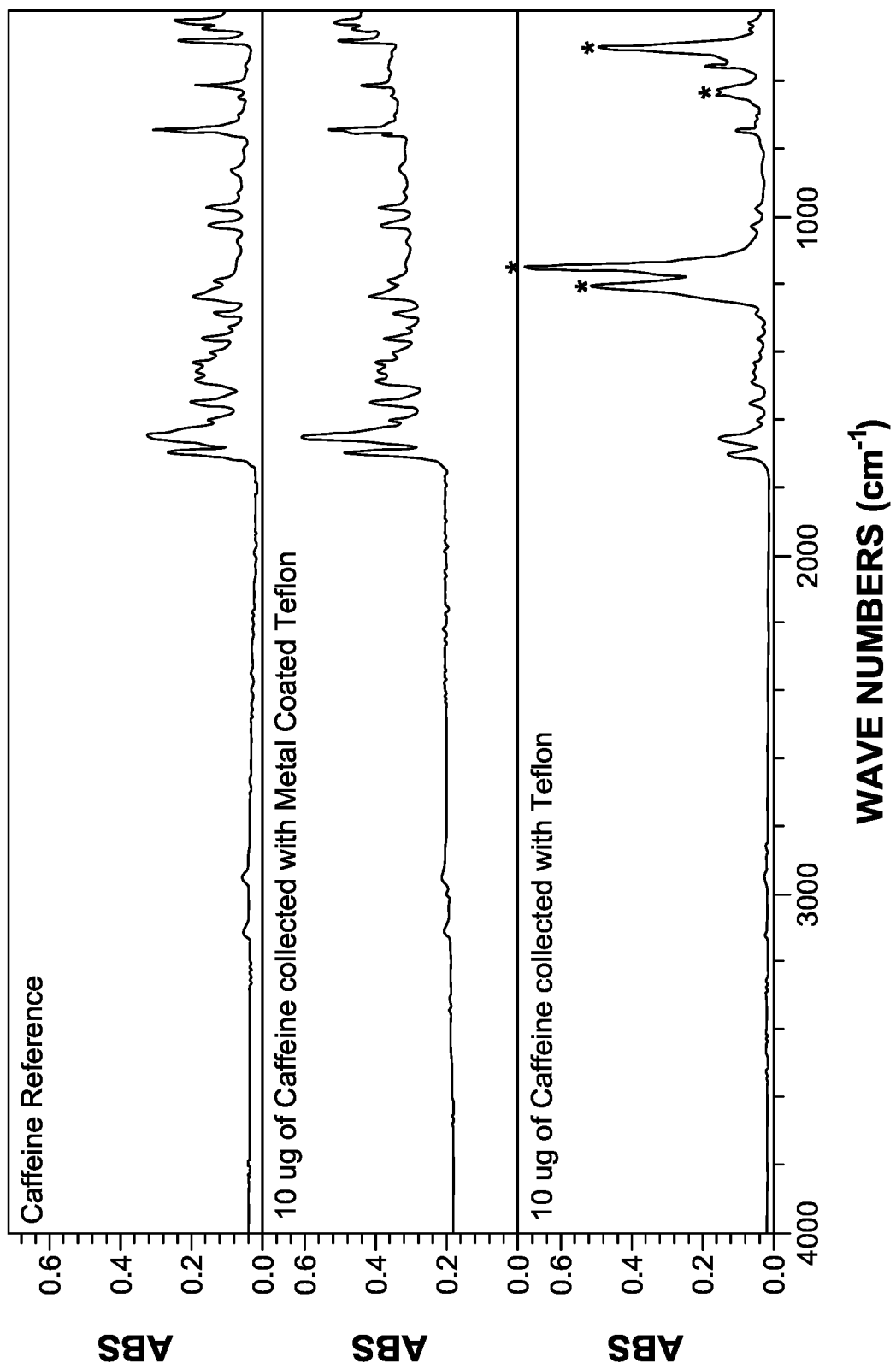
FIG. 16 is a graphical representation of an IR spectrum comparison obtained with ATR IR spectroscopy for caffeine powder captured on a polymer membrane and on a metal-coated polymer membrane.

In this experiment, a known concentration of caffeine powder+methanol was prepared, where 10 µg of caffeine was pipetted from this solution and dispersed onto a round-bottom mortar to form a faint residue approximately 1 cm$^2$ in area once the methanol evaporated. Caffeine residues were prepared and sampled in this manner with both the Teflon membrane and the metal coated Teflon membrane sampling material. Each sampling material was then analyzed using an ATR-FTIR spectrometer equipped with a single bounce diamond ATR crystal and anvil press. The results are shown in the Figure below, along with a reference spectrum of pure Caffeine. As shown in FIG. 16, the caffeine residue collected and analyzed with the metal coated Teflon membrane sampling material produces an accurate spectral match with the reference spectrum. By contrast, the caffeine residue collected and analyzed with the uncoated Teflon membrane sampling material shows a mixture of caffeine and Teflon absorption bands (the Teflon bands are labeled with asterisks in FIG. 16) and is therefore not an accurate match with the caffeine reference.

The present invention provides an improved apparatus for capturing analytes to be detected from fluids including gas and liquid fluids. Those skilled in the art will recognize, or be able to ascertain using no more than routine experimentation, many equivalents to the specific embodiments of the invention described by the following claims.

What is claimed is:

1. An apparatus for capturing a target analyte located on a surface, the apparatus comprising:
   a. a collection substrate formed with a border portion and a centered hub extending above a surface of the border portion to concentrate the target analyte from the surface thereon;
   b. an optical substrate made of ATR crystal material and configured to receive the target analyte from the collection substrate, wherein the centered hub of the collection substrate is configured with dimensions to match substantially a surface area of the optical substrate made of the ATR crystal material; and
   c. a facilitating housing configured to retain thereto and support the collection substrate sufficiently to enable analysis with an optical spectroscopy tool of the target analyte on the collection substrate.

2. The apparatus of claim 1 wherein the collection substrate is a glass fiber membrane.

3. The apparatus of claim 1 wherein the collection substrate is a membrane including nanoparticles selected for their affinity to the target analyte.

4. The apparatus of claim 1 wherein the collection substrate is fabricated of a mesh material.

5. The apparatus of claim 4 wherein the mesh material is a stainless steel mesh.

6. The apparatus of claim 1 wherein the collection substrate is a metal-coated polymer membrane.

7. The apparatus of claim 1 wherein the collection substrate is fabricated of polyethylene.

8. The apparatus of claim 1 wherein the facilitating housing is in a donut arrangement having a primary structural body spacing a first retaining ring from a second retaining ring.

9. The apparatus of claim 1 further comprising a handle connected to the facilitating housing, wherein the handle is of adjustable length and angle.

* * * * *